United States Patent
Dénarié et al.

(10) Patent No.: US 11,766,239 B2
(45) Date of Patent: Sep. 26, 2023

(54) ULTRASOUND IMAGING SYSTEM AND METHOD FOR LOW-RESOLUTION BACKGROUND VOLUME ACQUISITION

(71) Applicant: GE Precision Healthcare LLC, Wauwatosa, WI (US)

(72) Inventors: Bastien Emmanuel Dénarié, Nesøya (NO); Thor Andreas Tangen, Oslo (NO); Anders R. Sørnes, Oslo (NO)

(73) Assignee: GE Precision Healthcare LLC, Wauwatosa, WI (US)

( * ) Notice: Subject to any disclaimer, the term of this patent is extended or adjusted under 35 U.S.C. 154(b) by 173 days.

(21) Appl. No.: 17/186,614

(22) Filed: Feb. 26, 2021

(65) Prior Publication Data
US 2022/0273260 A1   Sep. 1, 2022

(51) Int. Cl.
*A61B 8/14* (2006.01)
*G06N 3/02* (2006.01)
*A61B 8/08* (2006.01)
*A61B 8/00* (2006.01)

(52) U.S. Cl.
CPC ............ *A61B 8/145* (2013.01); *A61B 8/0883* (2013.01); *A61B 8/461* (2013.01); *G06N 3/02* (2013.01)

(58) Field of Classification Search
CPC ....... A61B 8/145; A61B 8/0883; A61B 8/461; G06N 3/02
See application file for complete search history.

(56) References Cited

U.S. PATENT DOCUMENTS

| | | | |
|---|---|---|---|
| 2005/0228280 A1* | 10/2005 | Ustuner | A61B 8/483 600/443 |
| 2007/0238999 A1* | 10/2007 | Specht | A61B 8/0891 600/437 |
| 2009/0156937 A1* | 6/2009 | Sasaki | A61B 8/483 600/447 |
| 2016/0135790 A1* | 5/2016 | Von Ramm | A61B 8/145 600/447 |
| 2016/0213258 A1* | 7/2016 | Lashkari | G01S 15/8915 |
| 2016/0262720 A1* | 9/2016 | Henderson | A61B 8/466 |
| 2020/0074625 A1* | 3/2020 | Østvik | G16H 30/40 |
| 2020/0352542 A1* | 11/2020 | Errico | A61B 8/0891 |

FOREIGN PATENT DOCUMENTS

EP    1224621 A1 *   7/2002   ............. A61B 34/20

OTHER PUBLICATIONS

Shen et al., Ultrasound Baseband Delay-Multiply-and-Sum (BB-DMAS) nonlinear beamforming, Ultrasonics, vol. 96, Jul. 2019, pp. 165-174, https://doi.Org/10.1016/j.ultras.2019.01.010 (Year: 2019).*

* cited by examiner

Primary Examiner — John Denny Li (57) ABSTRACT

An ultrasound imaging system and method includes acquiring low-resolution volume data with an ultrasound probe during the process of acquiring high-resolution slice data of a plane with the ultrasound probe. The ultrasound imaging system and method includes displaying an ultrasound image on a display device based on the high-resolution slice data, generating a low-resolution volume based on the low-resolution volume data, and implementing, with a processor, a neural network to calculate guidance information based on the low-resolution volume. The ultrasound imaging system and method includes automatically performing an action with the processor based on the guidance information.

25 Claims, 8 Drawing Sheets

ULTRASOUND IMAGING SYSTEM AND METHOD FOR LOW-RESOLUTION BACKGROUND VOLUME ACQUISITION

FIELD OF THE INVENTION

This disclosure relates generally to a method and ultrasound imaging system for acquiring low-resolution volume data with an ultrasound probe during the process of acquiring high-resolution slice data with an ultrasound probe. The method and system further relates to calculating guidance information based on the low-resolution volume data and automatically performing an action based on the guidance information.

BACKGROUND OF THE INVENTION

Diagnostic ultrasound imaging is an imaging modality capable of displaying ultrasound images based on signals detected in response to transmitted ultrasound signals. An ultrasound image generated based on slice data is typically refreshed each time an additional frame of slice data is acquired. This provides clinicians with real-time images of the patient's anatomy. For many applications, such as echocardiography, it is necessary to obtain one or more standard views such as a parasternal long axis view, a parasternal short axis view, an apical four-chamber view, an apical two-chamber view, an apical three-chamber view, an apical five-chamber view, a subcostal four-chamber view, etc. In order to make an accurate clinical diagnosis and/or to obtain accurate measurements of a patient's anatomy from the standard view, it is necessary to correctly obtain the desired standard view. If the clinician accidentally acquires slice data from an incorrect plane, any measurements or quantitative data obtained from the image may be inaccurate. Likewise, if the clinician accidentally acquires slice data from an incorrect plane, it may be difficult or impossible to make an accurate clinical diagnosis since the image does not represent the standard view.

In echocardiography, for example, the slice plane for each of the apical views should pass through the apex of the heart. However, it is oftentimes difficult for the clinician to accurately position the slice plane to include the apex. Attempts to acquire apical views that do not include the apex of the heart are said to be foreshortened. It can be very difficult for clinicians, particularly relatively inexperienced clinicians, to identify that the image of the heart has been foreshortened from a single image.

Therefore, for these and other reasons, an improved ultrasound imaging system and method of ultrasound imaging is desired.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes acquiring low-resolution volume data with an ultrasound probe during the process of acquiring high-resolution slice data of a plane with the ultrasound probe. The method includes displaying an ultrasound image on a display device based on the high-resolution slice data, generating a low-resolution volume based on the low-resolution volume data, and implementing, with a processor, a neural network to calculate guidance information based on the low-resolution volume. The method includes automatically performing at least one of the following actions with a processor based on the guidance information: displaying a guidance suggestion for adjusting the ultrasound probe in order to obtain a desired view; adjusting steering parameters of the ultrasound probe in order to acquire the desired view with the ultrasound probe in a current position and orientation; providing a warning that the ultrasound probe is incorrectly positioned; or automatically placing a region-of-interest with respect to the ultrasound image.

In another embodiment, an ultrasound imaging system includes an ultrasound probe, a user interface, a display device, and a processor in electronic communication with the ultrasound probe, the user interface, and the display device. The processor is configured to control the ultrasound probe to acquire low-resolution volume data during the process of acquiring high-resolution slice data of a plane, display an ultrasound image on the display device based on the high-resolution slice data, and generate a low-resolution volume based on the low-resolution volume data. The processor is configured to implement a neural network to calculate guidance information based on the low-resolution volume. The processor is configured to automatically perform at least one of the following actions based on the guidance information: display a guidance suggestion for adjusting the ultrasound probe in order to obtain a desired view; adjust steering parameters of the ultrasound probe in order to acquire the desired view with the ultrasound probe in a current position and orientation; provide a warning that the ultrasound probe is incorrectly positioned; or place a region-of-interest with respect to the ultrasound image.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
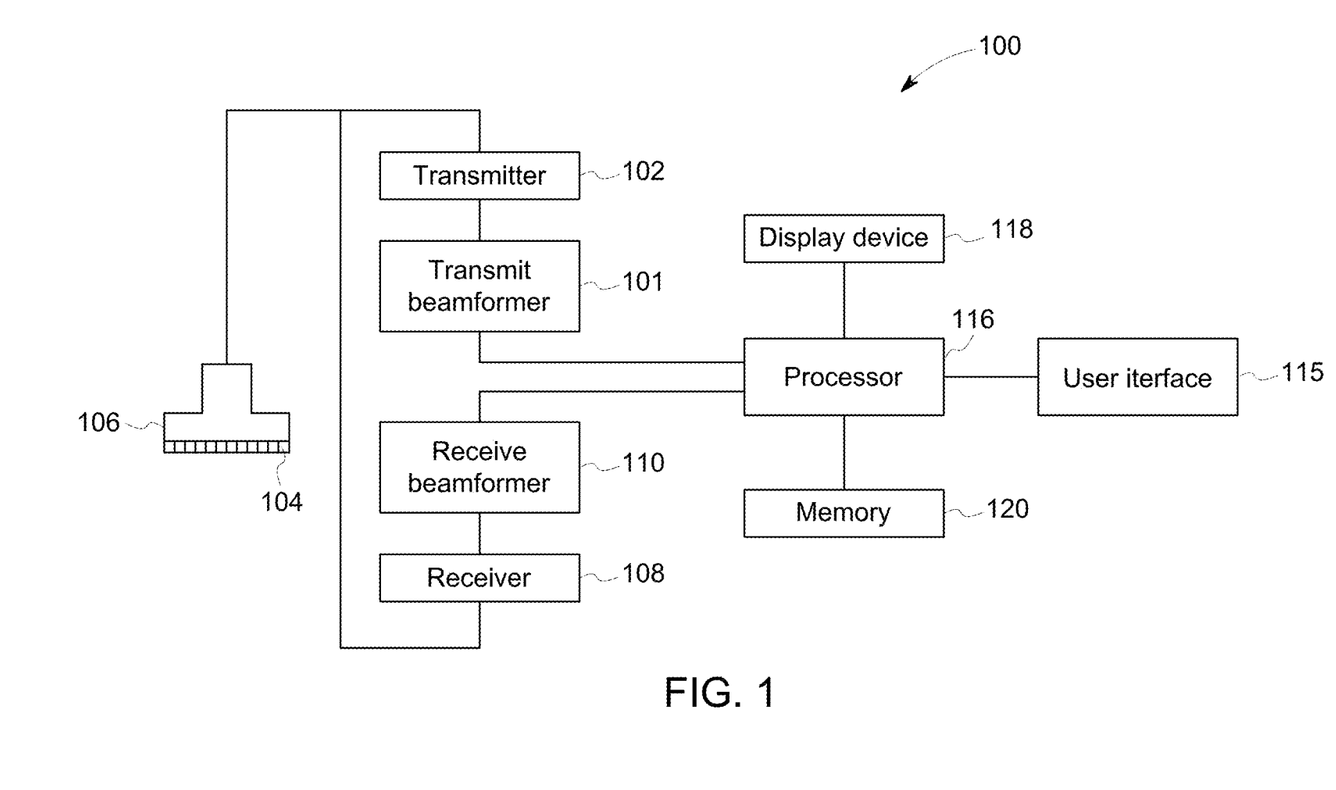
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within an ultrasound probe 106 to emit pulsed ultrasonic signals into a patient (not shown). The probe 106 is capable of volume acquisitions. According to an embodiment, the ultrasound probe 106 may be an 2D matrix array probe capable of full beamforming in both the azimuth and elevation directions. According to other embodiments, the ultrasound probe 106 may be a mechanical 3D/4D probe including an array of elements configured to be moved with respect to the rest of the ultrasound probe 106. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the ultrasound probe 106 may contain electronic circuitry to do all or part of the transmit beamforming and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The terms "data" and "ultrasound data" may be used in this disclosure to refer to either one or more datasets acquired with an ultrasound imaging system. A user interface 115 may be used to control operation of the ultrasound imaging system 100. The user interface 115 may be used to control the input of patient data, or to select various modes, operations, and parameters, and the like. The user interface 115 may include a one or more user input devices such as a keyboard, hard keys, a touch pad, a touch screen, a track ball, rotary controls, sliders, soft keys, or any other user input devices. The user interface is in electronic communication with the processor 116.

The ultrasound imaging system 100 also includes a processor 116 to control the transmit beamformer 101, the transmitter 102, the receiver 108 and the receive beamformer 110. As will be described in more detail hereinafter, some or all of the processor 116 may be implemented as a neural network in order to perform one or more tasks. The receive beamformer 110 may be either a conventional hardware beamformer or a software beamformer according to various embodiments. If the receive beamformer 110 is a software beamformer, it may comprise one or more of the following components: a graphics processing unit (GPU), a microprocessor, a central processing unit (CPU), a digital signal processor (DSP), or any other type of processor capable of performing logical operations. The beamformer 110 may be configured to perform conventional beamforming techniques as well as software beamforming techniques such as, for example, retrospective transmit beamforming (RTB).

The processor 116 may be one or more central processing units (CPUs), microprocessors, microcontrollers, graphics processing units (GPUs), digital signal processors (DSP), and the like. According to some embodiments, the processor may include one or more GPUs, where some or all of the one or more GPUs include a tensor processing unit (TPU). According to embodiments, the processor 116 may includes a field-programmable gate array (FPGA), or any other type of hardware capable of carrying out processing functions. The processor 116 may be an integrated component or it may be distributed across various locations. For example, according to an embodiment, processing functions may be split between two or more processors based on the type of operation. For example, embodiments may include a first processor configured to perform a first set of operations and a second, separate processor to perform a second set of operations. According to embodiments, one of the first processor and the second processor may be configured to implement a neural network. The processor 116 may be configured to execute instructions accessed from a memory. According to an embodiment, the processor 116 is in electronic communication with the ultrasound probe 106, the receiver 108, the receive beamformer 110, the transmit beamformer 101, and the transmitter 102. The processor 116 may control the ultrasound probe 106 to acquire ultrasound data. The processor 116 controls which of the elements 104 are active and the shape of a beam emitted from the ultrasound probe 106. The processor 116 is also in electronic communication with a display device 118, and the processor 116 may process the ultrasound data into images for display on the display device 118. For purposes of this disclosure, the term "electronic communication" may be defined to include both wired and wireless connections. According to other embodiments, the processor 116 may include multiple electronic components capable of carrying out varying processing functions. According to embodiments, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. Real-time frame rates may vary based on the size of the region or volume from which data is acquired and the specific parameters used during the acquisition. The data may be stored temporarily in a buffer (not shown) during a scanning session and processed in less than real-time in a live or off-line operation. For embodiments where the receive beamformer 110 is a software beamformer, the processing functions attributed to the processor 116 and the software beamformer hereinabove may be performed by a single processor such as the receive beamformer 110, the processor 116, a portion of the processor 116, or a separate processor according to various embodiments. Or, the processing functions attributed to the processor 116 and the beamformer 110 may be allocated in a different manner between any number of separate processing components.

Certain embodiments provide a non-transitory computer readable medium having stored thereon, a computer program having at least one code section. The at least one code section may be executable by the processor 116 for causing the ultrasound imaging system 100 to perform steps of any of the methods and/or functions described in this application.

According to an embodiment, the ultrasound imaging system 100 may continuously acquire ultrasound data at a frame-rate of, for example, 10 Hz to 30 Hz. Images generated from the data may be refreshed at a similar frame-rate. Other embodiments may acquire ultrasound data and display ultrasound images at different frame-rates. For example, some embodiments may acquire ultrasound data at a frame-rate of less than 10 Hz or greater than 30 Hz depending on the size of the volume and the intended application. For example, many applications involve acquiring ultrasound data at a frame rate of 50 Hz or more. A memory 120 is included for storing processed frames of acquired data. In an exemplary embodiment, the memory 120 is of sufficient capacity to store frames of ultrasound data acquired over a period of time of at least several seconds in length. The frames of data are stored in a manner to facilitate retrieval thereof according to its order or time of acquisition. The memory 120 may be Random Access Memory (RAM) or other dynamic storage device. The memory may be a hard drive, a solid-state drive, flash memory, or any other known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., bi-plane mode, tri-plane mode, B-mode, color Doppler, M-mode, color M-mode, spectral Doppler, Elastography, TVI, strain, strain rate, and the like) to form 2D or 3D data. For example, one or more modules may generate bi-plane mode, tri-plane mode, B-mode, color Doppler, M-mode, color M-mode, spectral Doppler, Elastography, TVI, strain, strain rate and combinations thereof, and the like. The image beams and/or frames are stored, and timing information indicating a time at which the data was acquired in memory may be recorded. The modules may include, for example, a scan conversion module to perform scan conversion operations to convert the image frames from beam space coordinates to display space coordinates. A video processor module may be provided that reads the image frames from a memory, such as the memory 120, and displays the image frames in real time while a procedure is being carried out on a patient. A video processor module may store the image frames in an image memory, from which the images are read and displayed.

Figure 2:
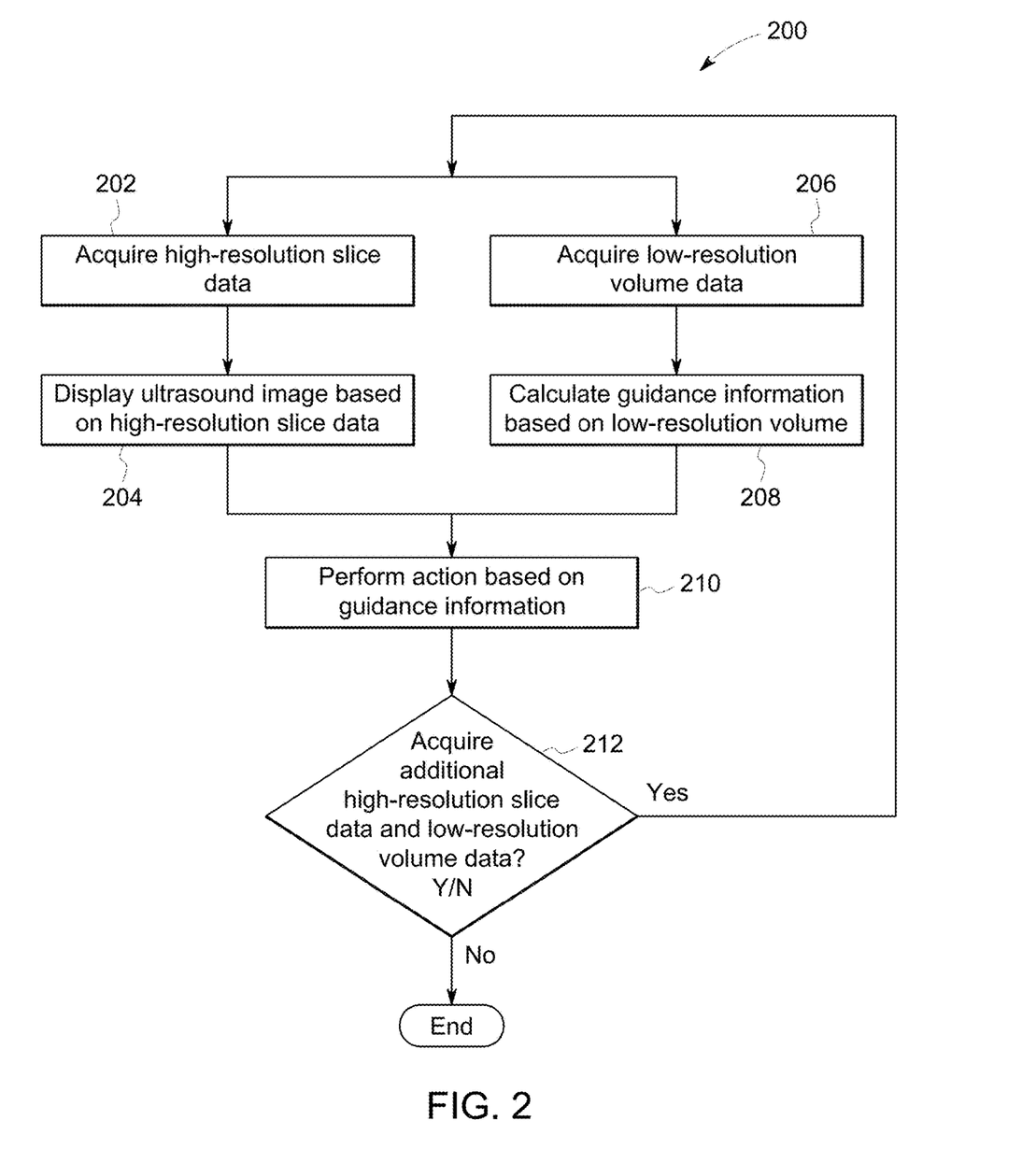
FIG. 2 is a flow chart of a method in accordance with an embodiment.

FIG. 2 is a flow chart of a method 200 in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 2. Due to the nature of the method 200, some of the steps shown in FIG. 2 may be performed at the same time or during overlapping periods of time. The method 200 will be described in accordance with an exemplary embodiment where the method 200 is performed by the ultrasound imaging system 100 shown in FIG. 1. The technical effect of the method 200 is the automatic performance of an action based on guidance information calculated from a low-resolution volume.

Figure 3:
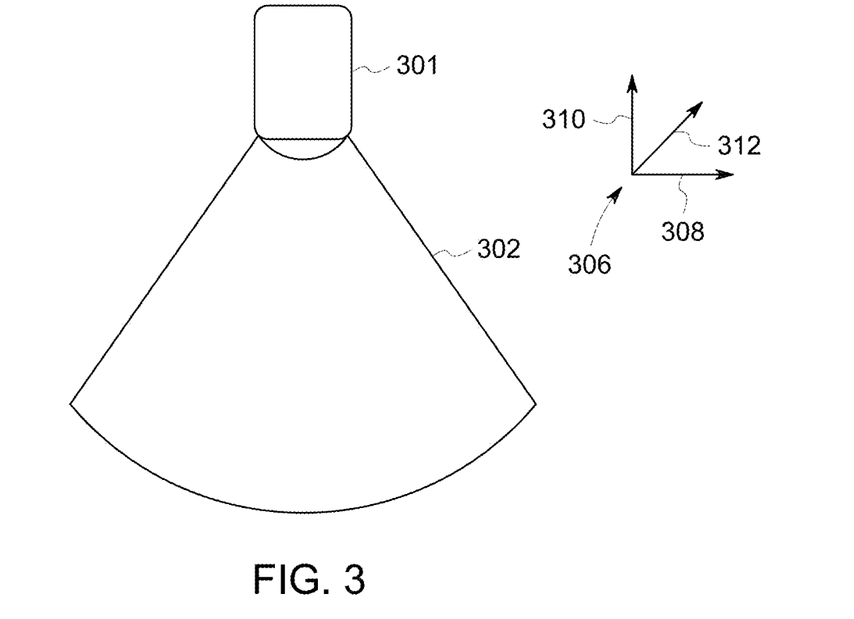
FIG. 3 is a representation of an ultrasound probe and a planar region in accordance with an embodiment.
Figure 4:
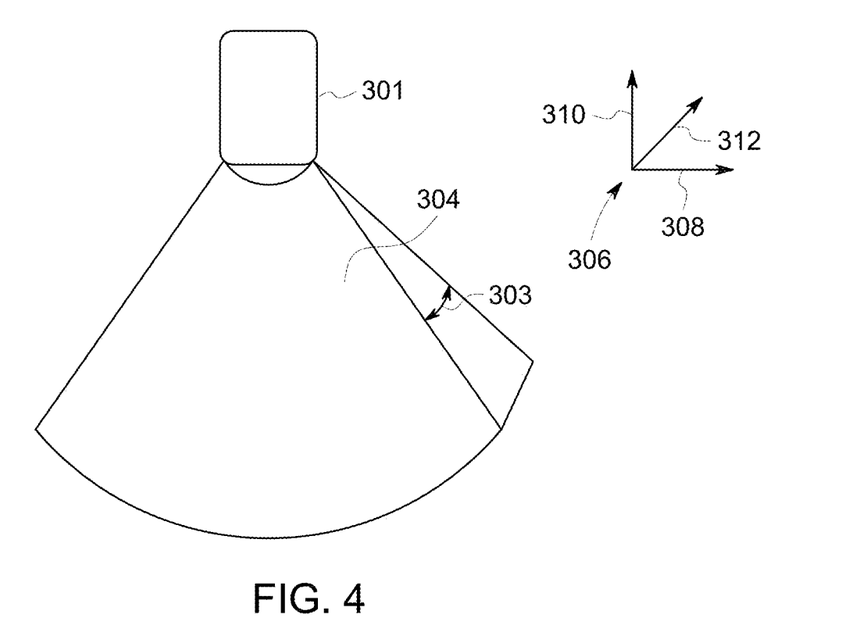
FIG. 4 is a representation of an ultrasound probe and a thin slab in accordance with an embodiment.

The method 200 will be described with respect to both FIG. 1 and FIG. 2. At step 202, the processor 116 controls the ultrasound probe 106 to acquire high-resolution slice data from a patient. The high-resolution slice data may be 2D ultrasound data acquired from a planar or generally planar region or the high-resolution slice data may be ultrasound data acquired from a thin slab. 2D ultrasound data includes a thickness of a single sample in a direction perpendicular to the acquisition plane. A thin slab, on the other hand, includes a thickness of greater than a single sample in a direction perpendicular to the acquisition plane. FIG. 3 is a schematic representation of an ultrasound probe 301 and a planar region 302 according to an embodiment. FIG. 3 includes a coordinate axis 306. The coordinate axis 306 represents an azimuth direction 308, a depth direction 310, and an elevation direction 312. The high-resolution slice data may be 2D ultrasound data acquired from the planar region 302. FIG. 4 is a schematic representation of the ultrasound probe 301, and a thin slab 304. According to an embodiment, the high-resolution slice data may be acquired from a thin slab 304. The planar region 302 (shown in FIG. 3) is only the width of a single sample in the elevation direction 312. The thin slab 304, on the other hand, has a thickness greater than a single sample in the elevation direction in the example shown in FIG. 4. The thin slab 304 may be defined to have an opening angle 303 of 15 degrees or less. According to exemplary embodiments, the high-resolution slice data may include ultrasound data compounded from 2 or more planes that acquired from slightly different positions in the elevation direction 312.

At step 204, the processor 116 controls the display device 118 to display an ultrasound image based on the high-resolution slice data. According to an exemplary embodiment, the ultrasound image based on the high-resolution slice data may be a real-time ultrasound image. For example, the ultrasound image may be repeatedly refreshed to reflect the most-recently acquired frame of high-resolution slice data during the process of acquiring the high-resolution slice data.

Figure 5:
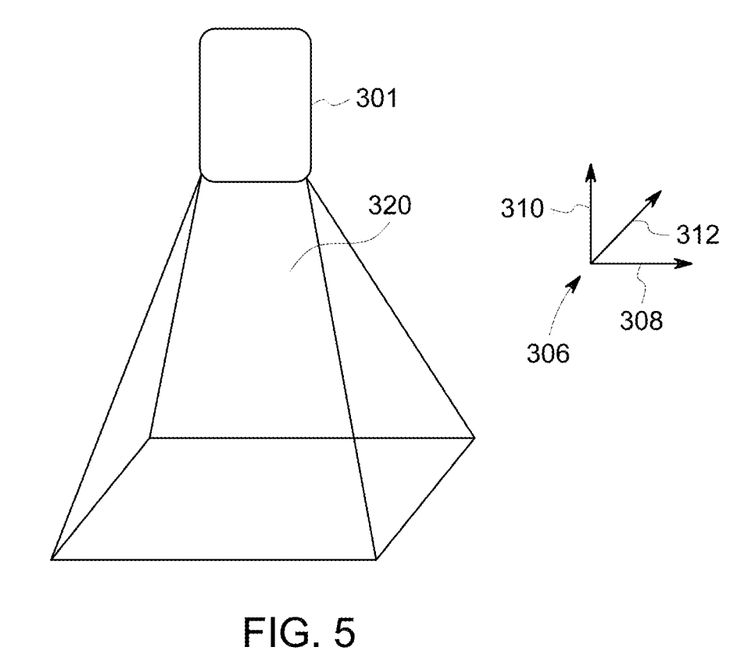
FIG. 5 is a representation of an ultrasound probe and a volume in accordance with an embodiment.

Steps 206 and 208 may be performed during the process of performing steps 202 and 204 according to an exemplary embodiment. At step 206, the processor 116 controls the ultrasound probe to acquire low-resolution volume data during the process of acquiring the high-resolution slice data during step 202. FIG. 5 is a schematic representation of the ultrasound probe 301 and a representation of a volume 320 from which the low-resolution volume data may be acquired. The processor 116 may be configured to alternate between acquiring one or more frames of high-resolution slice data and acquiring one or more frames of low-resolution volume data while performing steps 202 and 206. For example, according to an exemplary embodiment, the processor 116 may be configured to control the ultrasound probe 106 to acquire a frame of low-resolution volume data between two adjacent frames of the high-resolution slice data. According to other embodiments, the processor 116 may be configured to control the ultrasound probe 106 to acquire multiple frames of high-resolution slice data between each adjacent frame of low-resolution volume data.

According to other embodiments, the processor 116 may be configured to control the ultrasound probe 106 to interleave the acquisition of the low-resolution volume data with the acquisition of the high-resolution slice data while performing steps 202 and 206. For example, the processor 116 may control the ultrasound probe 106 to acquire low-resolution volume data based on one or more transmit lines transmitted during the process of acquiring a single frame of high-resolution slice data. Additional details about the various acquisition schemes for acquiring the high-resolution slice data and the low-resolution volume data will be described hereinafter.

An important aspect of this invention is that it allows for the acquisition of low-resolution volume data with a minimal impact on the image quality of the ultrasound image generated from the high-resolution slice data. Acquiring low-resolution volume data, as opposed to high-resolution volume data, reduces the total amount of acquisition time dedicated to the volume acquisition. This frees up time during the acquisition sequence for the acquisition of the high-resolution slice data. The intent of this invention is to use the low-resolution volume data to calculate guidance information. Since it is not intended for display, the low-resolution volume data can be of much lower resolution than convention high-resolution volume data. This, in turn, minimizes the impact on the resolution of the high-resolution slice data, which is intended to be displayed and used for diagnostic purposes.

In various embodiments, the low-resolution volume data may be acquired with a relatively small number of transmit events compared to a conventional volume acquisition. For example, according to an embodiment, the low-resolution volume data may be acquired with 25 transmit events or less. The 25 transmit events, may, for instance, correspond with a 5×5 transmit pattern in the azimuth direction 308 and the elevation direction 312. According to other embodiments, the low-resolution volume data may be acquired with less than 16 transmit events. The 16 transmit events, may, for instance, correspond with a 4×4 transmit pattern in azimuth direction 308 and the elevation direction 312. In other embodiments, the transmit events may be distributed in an irregular or staggered pattern. For example, the transmit events in adjacent rows in the elevation direction 312 may be offset in the azimuth direction 308. It should be appreciated that other embodiments may use a different number of transmit events and/or the transmit events may be arranged in different transmit patterns. For example, embodiments may use a different number of transmit events in the elevation and azimuth directions.

The processor 116 may be configured to acquire the low-resolution volume data at step 206 using defocused transmit events. For example, the processor 116 may be configured to transmit defocused waves for each of the transmit events. Each defocused transmit event covers a larger field-of-view than a conventional focused transmit event. Using defocused transmit events helps to acquire more samples in the volume while using a smaller number of transmit events. As discussed previously, using fewer transmit events results in less total time spent acquiring the low-resolution volume data, which enables more time and resources to be spent on acquiring the high-resolution slice data and generating the ultrasound image based on the high-resolution slice data.

The processor 116 may be configured to beamform the low-resolution volume data and/or the high-resolution slice data using nonlinear beamforming techniques according to embodiments where the receive beamformer 110 is a software beamformer. Linear beamforming techniques typically include delay-and-sum beamforming. Nonlinear beamforming techniques may include delay-multiply-and-sum or applying any other nonlinear operations during the process of beamforming the low-resolution volume or the high-resolution slice data. Nonlinear beamforming techniques may be used to reduce the level of side lobes that would otherwise result from transmitting defocused transmit beams. Nonlinear beamforming technique may therefore help recover some spatial resolution due to the relatively low number of transmit events used to acquire the low-resolution volume data.

According to an embodiment, the receive beamformer 110 may be configured to apply a massively multiline beamforming technique to the low-resolution volume data acquired along each transmit line. Using a massively multiline beamforming technique may be particularly advantageous for embodiments that use a relatively small number of transmit events. Massively multiline beamforming techniques acquire data along more than 16 receive lines for each transmit line. According to an exemplary embodiment, the receive beamformer 110 may beamform 32 or more receive lines for each transmit line. According to yet other embodiments, the receive beamformer 110 may be configured to beamform 64 or more receive lines for each transmit line.

The low-resolution volume data may be of lower temporal resolution either in addition to or instead of being of lower spatial resolution. For example, conventional volume acquisitions may have frame rates that vary between roughly 20 frames-per-second (FPS) and 70 FPS. The low-resolution volume data may, for instance be acquired at a much lower frame rate. For example, according to some embodiments, acquiring the low-resolution volume data at between a frame rate between 0.25 and 10 FPS may be sufficient. In other embodiments, the low-resolution frame rate may be higher than 10 FPS. According to an embodiment, the frame rate (i.e., the temporal resolution) and the spatial resolution of the low-resolution volume data may be inversely related. That is, embodiments using low-resolution volume data with a relatively low spatial resolution may have a relatively high frame rate; and embodiments using low-resolution volume data with a relatively high spatial resolution may have a relatively low frame rate.

Based on the descriptions above, it should be appreciated that for the purposes of this application the term "low-resolution volume data" may be defined to include volume data that has a lower resolution than the high-resolution slice data; volume data that is acquired with a lower number of transmit events than a conventional volume data acquisition or volume data that is acquired with a frame rate that is lower than a convention volume data acquisition. It should be appreciated that the low-resolution volume data may include different combinations of spatial resolution and temporal resolution based on the type of acquisition and the amount of image quality compromise that is acceptable for the high-resolution slice data.

As discussed previously, according to various embodiments, the processor 116 may be configured to acquire the low-resolution volume data in an interleaved manner with the high-resolution slice data. According to an embodiment, one or more transmit events used for the low-resolution volume acquisition may be transmitted during the process of acquiring a single frame of the high-resolution slice data. One or more additional transmit events for the low-resolution volume may be transmitted during the process of acquiring a subsequent frame of high-resolution slice data. Using this technique, the frame of low-resolution volume data will not be completely acquired until all of the different transmit events for the volume have been transmitted. Interleaving only a subset of the transmit lines during the process of acquiring a single frame of high-resolution slice data minimizes the time penalty on each frame of high-resolution slice data. For example, according to an embodiment where only 4 transmits events are interleaved with the acquisition of the transmit events for each frame of high-resolution slice data, the elapsed acquisition time for each frame of high-resolution slice data is only extended by the time it takes to transmit the 4 transmit events and receive data based on the 4 transmit events. Likewise for an embodiment where only one transmit event is interleaved with the acquisition of each frame of high-resolution slice data, the elapsed acquisition time for each frame of high-resolution slice data is only extended by the time it takes to transmit the one transmit event and receive data based on the one transmit event.

According to an embodiment, the transmit events for the acquisition of the low-resolution volume data may be spread evenly across the transmit sequence for each frame of high-resolution slice data. This interleaving technique may result in a slight loss of coherency due to the additional time between adjacent transmit events for the high-resolution slice data due to the addition of the transmit event/s for the low-resolution volume data.

According to an embodiment, the transmit events for the low-resolution volume may be distributed randomly between the transmit events for each frame of the high-resolution slice data. The random distribution of the transmit events for the low-resolution volume may be modified from frame-to-frame so that the transmit events for the low-resolution volume data are positioned at different times/locations in the transmit sequence for adjacent or consecutive frames of the high-resolution slice data to minimize the visual impact caused by a loss of coherence due to the interleaving. According to an embodiment, the low-resolution volume data is not displayed as an image. In order to minimize the impact on the high-resolution slice data, it is anticipated that the resolution of the low-resolution volume data would be too low for display. The low-resolution volume data is "background" data as it is not intended for display.

At step 208, the processor 116 calculates guidance information based on the low-resolution volume generated from the low-resolution volume data. According to an embodiment, the processor 116 may implement a neural network in order to calculate the guidance information. Additional information about the calculation of guidance information will be discussed hereinafter.

Figure 6:
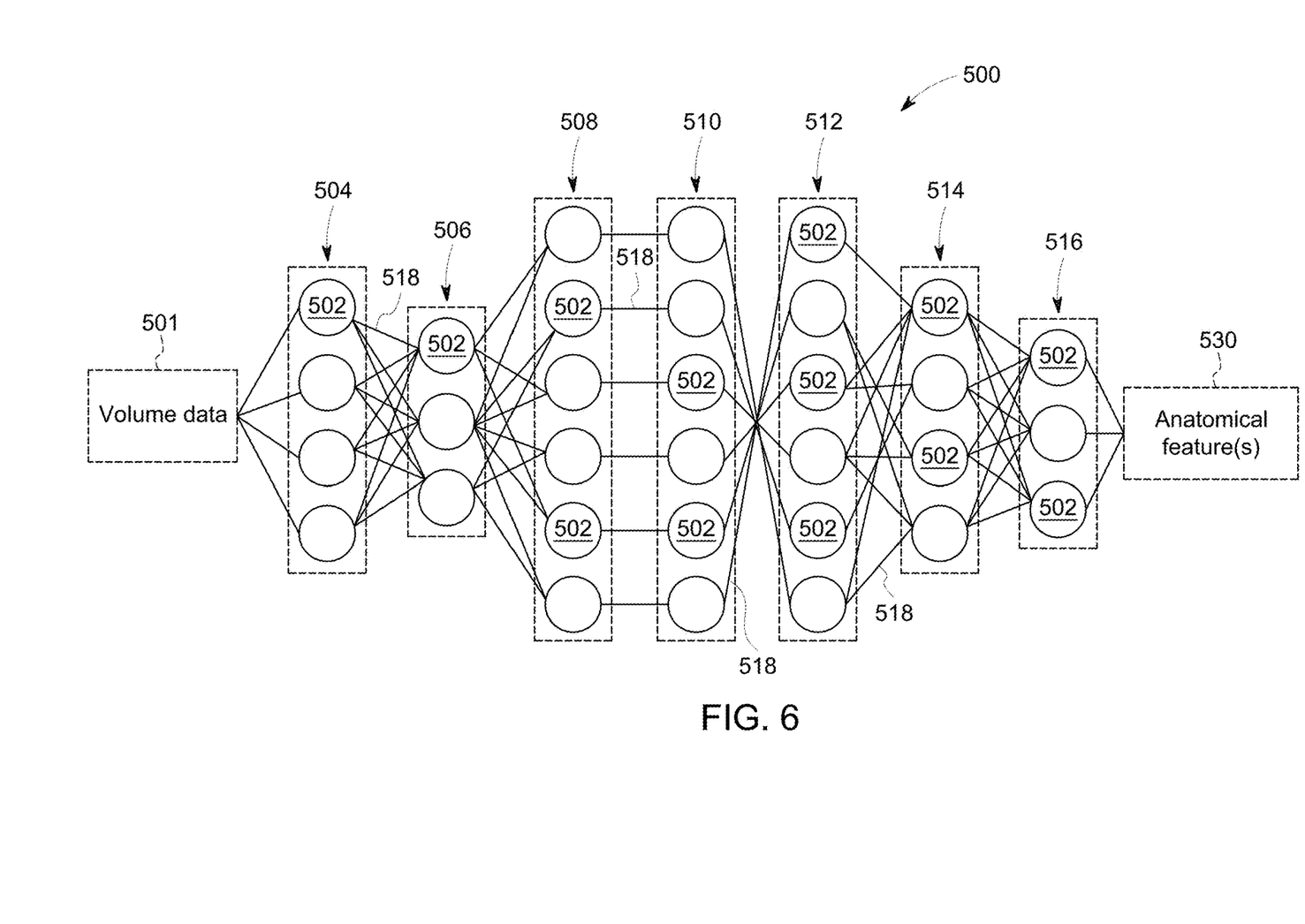
FIG. 6 is a schematic diagram of a neural network in accordance with an embodiment.
Figure 7:
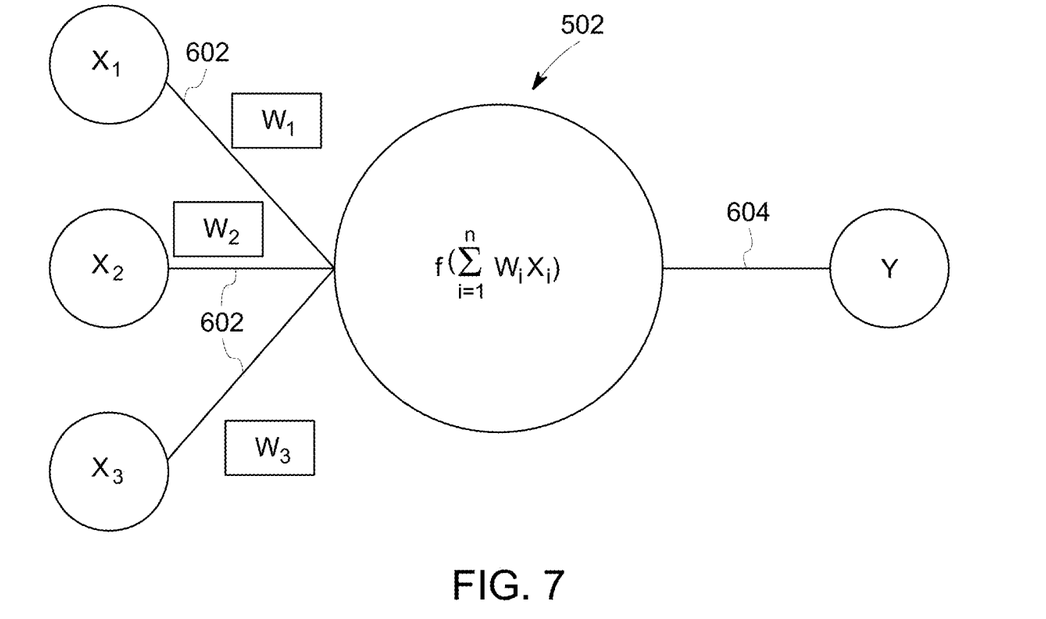
FIG. 7 is a schematic diagram showing input and output connections for a neuron of a neural network in accordance with an exemplary embodiment.

Referring now to FIGS. 6 and 7, an exemplary neural network in accordance with an exemplary embodiment is shown. In some examples, the neural network may be trained with training sets of volume data. According to other embodiments, the neural network may be trained with both a set of low-resolution volume data and a set of high-resolution volume data.

FIG. 6 depicts a schematic diagram of a neural network 500 having one or more nodes/neurons 502 which, in some embodiments, may be disposed into one or more layers 504, 506, 508, 510, 512, 514, and 516. Neural network 500 may be a deep neural network. As used herein with respect to neurons, the term "layer" refers to a collection of simulated neurons that have inputs and/or outputs connected in similar fashion to other collections of simulated neurons. Accordingly, as shown in FIG. 6, neurons 502 may be connected to each other via one or more connections 518 such that data may propagate from an input layer 504, through one or more intermediate layers 506, 508, 510, 512, and 514, to an output layer 516. The one or more intermediate layers 506, 508, 510, 512, and 514 are sometimes referred to as "hidden layers."

FIG. 7 shows input and output connections for a neuron in accordance with an exemplary embodiment. As shown in FIG. 7, connections (e.g., 518) of an individual neuron 502 may include one or more input connections 602 and one or more output connections 604. Each input connection 602 of neuron 502 may be an output connection of a preceding neuron, and each output connection 604 of neuron 502 may be an input connection of one or more subsequent neurons. While FIG. 7 depicts neuron 502 as having a single output connection 604, it should be understood that neurons may have multiple output connections that send/transmit/pass the same value. In some embodiments, neurons 502 may be data constructs (e.g., structures, instantiated class objects, matrices, etc.), and input connections may be received by neuron 502 as weighted numerical values (e.g., floating point or integer values). For example, as further shown in FIG. 7, input connections X1, X2, and X3 may be weighted by weights W1, W2, and W3, respectively, summed, and sent/transmitted/passed as output connection Y. As will be appreciated, the processing of an individual neuron 502 may be represented generally by the equation:

$$Y = f\left(\sum_{i=1}^{n} W_i X_i\right)$$

where n is the total number of input connections 602 to neuron 502. In one embodiment, the value of Y may be based at least in part on whether the summation of WiXi exceeds a threshold. For example, Y may have a value of zero (0) if the summation of the weighted inputs fails to exceed a desired threshold.

As will be further understood from FIGS. 6 and 7, input connections 602 of neurons 502 in input layer 504 may be mapped to an input 501, while output connections 604 of neurons 502 in output layer 516 may be mapped to an output 530. As used herein, "mapping" a given input connection 602 to input 501 refers to the manner by which input 501 affects/dictates the value said input connection 602. Similarly, as also used herein, "mapping" a given output connection 604 to output 530 refers to the manner by which the value of said output connection 604 affects/dictates output 530.

Accordingly, in some embodiments, the acquired/obtained input 501 is passed/fed to input layer 504 of neural network 500 and propagated through layers 504, 506, 508, 510, 512, 514, and 516 such that mapped output connections 604 of output layer 516 generate/correspond to output 530. As shown, input 501 may include a low-resolution volume. The cardiac image may depict one or more structures that are identifiable by the neural network 500. Further, output 530 may include structures, landmarks, contours, or planes associated with standard views.

Neural network 500 may be trained using a plurality of training datasets. According to various embodiments, the neural network 500 may be trained with volume data. The neural network 500 may be trained with low-resolution volume data, high-resolution volume data, or a combination of low-resolution volume data and high-resolution volume data. Each training dataset may include volume data that are, for example, annotated. Based on the training datasets, the neural network 500 may learn to identify a plurality of structures from the volume data. The machine learning, or deep learning, therein (due to, for example, identifiable trends in placement, size, etc. of anatomical features) may cause weights (e.g., W1, W2, and/or W3) to change, input/output connections to change, or other adjustments to neural network 500. Further, as additional training datasets are employed, the machine learning may continue to adjust various parameters of the neural network 500 in response. As such, a sensitivity of the neural network 500 may be periodically increased, resulting in a greater accuracy of anatomical feature identification.

According to an embodiment, the neural network 500 may be trained to identify landmark structures in the volume data. For example, according to an embodiment where the volume data is cardiac data, the neural network 500 may be trained to identify structures such as the right ventricle, the left ventricle, the right atrium, the left atrium, one or more valves, such as the tricuspid value, the mitral valve, the aortic valve, the apex of the left ventricle, the septum, etc. The neural network 500, may, for instance, be trained with low-resolution volume data that has been annotated to identify one or more structures that may be used as landmarks. According to another embodiment, the neural network 500 may be trained using both low-resolution volume data and high-resolution volume data. The high-resolution volume data and the low-resolution volume data used for training may, for instance have been acquired in pairs from the same patient, ultrasound probe, and probe position and orientation. For example, one such pair may include a low-resolution volume dataset acquired from a first position and orientation and a high-resolution volume dataset acquired from the first position and orientation. By using the same ultrasound probe, the same patient, and the same position and orientation, the pair may differ primarily in the resolution of the data. The low-resolution volume data is closer to the data that would be acquired at step 206 in the method 200. However, additionally using high-resolution volume data to train the neural network 500 may lead to a greater level of accuracy in identifying structures due to the higher resolution of the data. Additionally, since the low-resolution volume data and the high-resolution volume data are paired, the neural network 500 is able to learn how a low-resolution volume dataset of a volume corresponds to a high-resolution volume dataset of the same volume.

According to an embodiment, the neural network 500 may be trained to identify the locations of one or more standard views based on the training data. A non-limiting list of exemplary standard views includes: parasternal long axis, parasternal short axis, apical four-chamber, apical two-chamber view, apical three-chamber view, apical five chamber view, and coronary sinus view. The processor 116 may identify the standard views using according to multiple techniques. According to an exemplary embodiment, the neural network 500 may be trained to identify the various standard views from the low-resolution volume. According to another embodiment, the processor 116 may by configured to identify the standard views using landmarks identified in the low-resolution volume with the neural network 500.

Referring back to step 208 of the method 200, the processor 116 calculates guidance information based on the low-resolution volume generated from the low-resolution volume data using the output of the neural network 500. As discussed hereinabove, according to some embodiments, the neural network 500 may determine the position of one or more landmark structures based on the low-resolution volume or the neural network 500 may determine the position of one or more standard views. Since the low-resolution volume data is acquired during the process of acquiring the high-resolution slice data, the low-resolution volume data is acquired from the same or from substantially the same position as the high-resolution slice data. According to many embodiments, the high-resolution slice data is displayed as a real-time ultrasound image. In other words, the low-resolution volume data will be acquired from a real-time position of the ultrasound probe 106. Based on the association between the ultrasound image being displayed, the low-resolution volume data acquired by the ultrasound probe 106, and the current position and orientation of the ultrasound probe 106, the guidance information may be used to provide feedback to help the clinician acquire the desired ultrasound data for a given clinical procedure.

Figure 8:
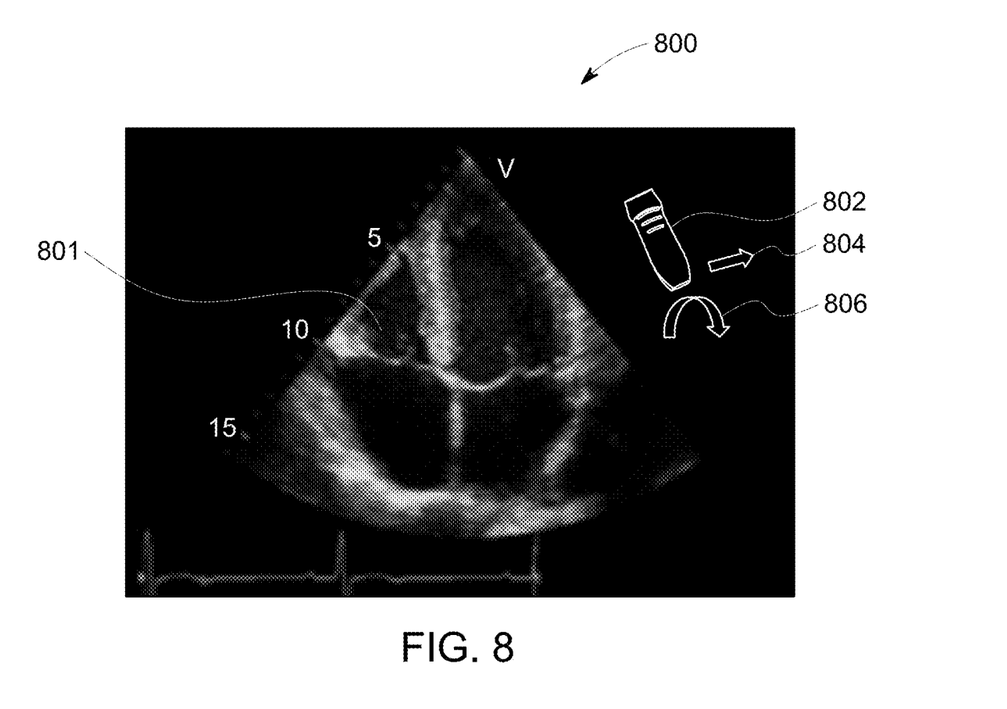
FIG. 8 is a screenshot in accordance with an exemplary embodiment.

At step 210 of the method 200, the processor 116 automatically performs an action based on the guidance information calculated at step 208. For example, according to an embodiment, the processor 116 may display a guidance suggestion on the display device 118 for adjusting the ultrasound probe 106 in order to obtain a desired view. The processor 116, may display the guidance suggestion by displaying text describing how the clinician should move the ultrasound probe 106, or by displaying one or more graphical icons indicating how the ultrasound probe 106 should be moved, or by a combination of displaying text and displaying one or more graphical icons indicating how the ultrasound probe 106 should be moved. The guidance suggestion may, for instance include directions related to one or more of translating the ultrasound probe 106, rotating the ultrasound probe 106 and tilting the ultrasound probe 106. For example, the graphical icons may include arrows or other directional indicators in order to convey the way that the ultrasound probe 106 should be adjusted in order to obtain the high-resolution slice data from of the desired view. According to various embodiments, the guidance suggestion may be displayed on the display device 118 along with an icon of the probe in order to help the clinician better understand how the ultrasound probe 106 should be adjusted to acquire the desired view. For example, FIG. 8 is a screenshot 800 including an ultrasound image 801, an icon of an ultrasound probe 802, and a first graphical icon 804, and a second graphical icon 806. The first graphical icon 804 is an arrow and it indicates that the ultrasound probe 106 should be tilted in the direction indicated by the arrow. The second graphical icon 806 is a curved arrow and it represents that he ultrasound probe 106 should be rotated in a clockwise direction as indicated by the curved arrow. Other embodiments may use different graphical icons and/or a different icon of the ultrasound probe in order to graphically convey how the ultrasound probe 106 should be moved (i.e., one or more of tilted, rotated, or translated) according to various embodiments.

According to an embodiment, the processor 116 may automatically perform an action based on the guidance information by automatically adjusting steering parameters of the ultrasound probe 106 in order to acquire the desired view with the ultrasound probe 106 in a current position and orientation. For example, the previous embodiment involved displaying a guidance suggestion instructing the clinician about how to adjust the position of the ultrasound probe 106 in order to acquire high-resolution slice data from the desired view and/or that includes a desired anatomical region. Instead of providing instructions for adjusting the ultrasound probe 106, the processor 116 may instead adjust the steering parameters of the ultrasound probe 106 in order to acquire additional high-resolution slice data from a plane or slab with a different geometrical relationship to the ultrasound probe than the previously acquired high-resolution slice data. For instance, the processor 116 may control the ultrasound probe 106 to acquire additional high-resolution slide data from a plane or slab with one or more of a different tilt or rotation with respect to the ultrasound probe 106. The processor 116 may, for instance, calculate the adjustments to the ultrasound probe's current position and orientation in order for the high-resolution slice data to include the desired standard view based on low-resolution volume. For example, the processor 116 may use the outputs of the neural network 500 to identify the position of the standard view with respect to the low-resolution volume. Since the position of the current acquisition plane or slab is know with respect to the low-resolution volume, the processor 116 may then calculate the adjustments to the ultrasound probe 106 that are needed in order to acquire high-resolution slice data of the standard view.

Figure 9:
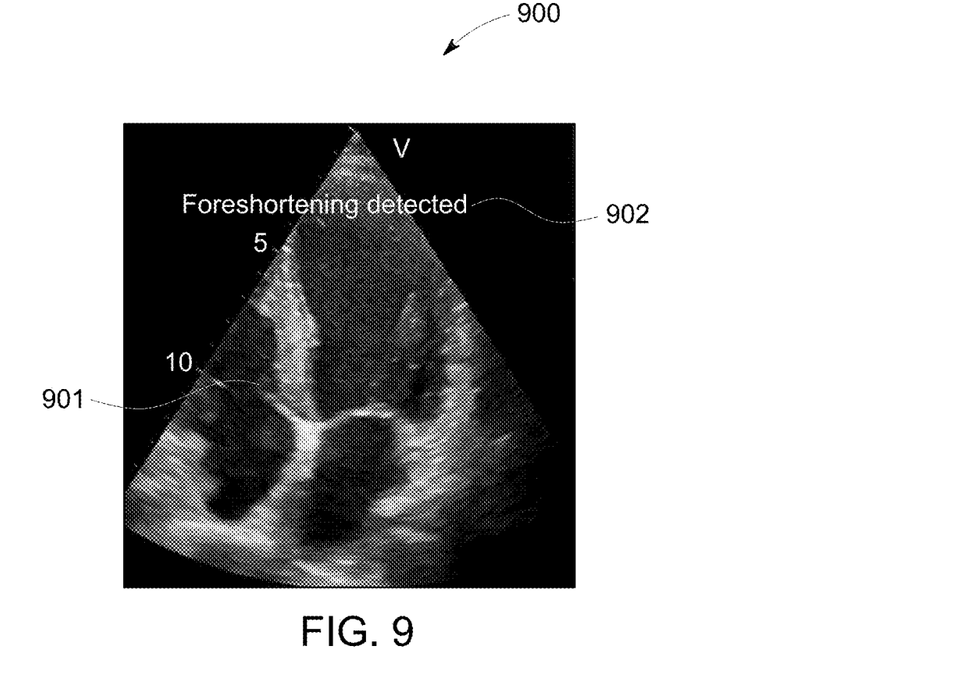
FIG. 9 is a screenshot in accordance with an exemplary embodiment.

According to an embodiment, the processor 116 may provide a warning that the ultrasound probe 106 is incorrectly positioned. For example, some standard views, such as the apical four-chamber view, are supposed to include the apex of the patient's heart. However, it can be difficult for a clinician, particularly a less-experienced clinician, to properly position the ultrasound probe in order to acquired high-resolution slice data of a plane that passes through the patient's apex. When an ultrasound image that is supposed to include the apex of the heart does not include the apex, it is said to be "foreshortened" since the left ventricle will appear shorter in the image than its true length. According to an embodiment, the neural network 500 may be configured to detect one or more structures from the low-resolution volume data and then, based on the output from the neural network 500, the processor 116 may determine if the current high-resolution slice view includes the apex of the heart or if it has been foreshortened. If the processor 116 determines that the current image has been foreshortened, the processor 116 may, for instance, display a warning that the ultrasound probe 106 is incorrectly positioned. For example, the processor 116 may display a notification, such as the words, "warning," "incorrect view," "foreshortening detected," or other warning notifications. FIG. 9 is a screenshot 900 according to an embodiment. The screenshot 900 includes an ultrasound image 901 and a notification 902, which is a text-based notification that states "foreshortening detected." Other embodiments may display different text-based notifications and/or they may provide a warning using other techniques. When the example shown in FIG. 9 is related to detecting foreshortening, it should be understood that different text-based notifications may be used to provide warnings associated with different views that may not involve foreshortening. Other embodiments may use an audible alarm or color to provide the warning that the ultrasound probe 106 is incorrectly positioned. As shown in FIG. 2, at step 212 the method may return to steps 202 and 206 if it is desired to acquire additional high-resolution slice data and additional low-resolution volume data. The method 200 may automatically return to steps 202 and 206 from step 212 as long as the clinician continues to acquire additional data (both high-resolution slice data and low resolution volume data) with the ultrasound probe 106. Once at steps 202 and 206, the method 200 may repeat through steps 202, 204, 206, 208, 210, and 212. With each iteration, the method 200 may display an ultrasound image based on the most-recently acquired high-resolution slice data and the processor 116 may calculate the guidance information based on the most recently acquired low-resolution volume data. The processor may therefore perform the action based on the guidance information at step 210 based on the most recently acquired low-resolution volume data that reflects the real-time or near real-time position and orientation of the ultrasound probe 106. As the method 200 is iteratively repeated, the processor 116 may update the guidance information, and the action that should be performed based on the guidance information, based on the current position and orientation of the ultrasound probe 106. For example, the clinician may be applying adjustments to one or both of the position and orientation of the ultrasound probe 106 as the method 200 is being performed. The processor 116 may be configured to provide an affirmative message when it is determined that the high-resolution slice data is being acquired of the desired plane. For example, the affirmative message may identify that the correct view has been acquired by displaying text on the display device 118 stating messages such as "correct view acquired," "four-chamber view acquired," or other affirmative messages. Or, the processor 116 may simply remove the warning that was displayed on the display device 118 when it is determined that the high-resolution slice data is being acquired of the desired plane.

Figure 10:
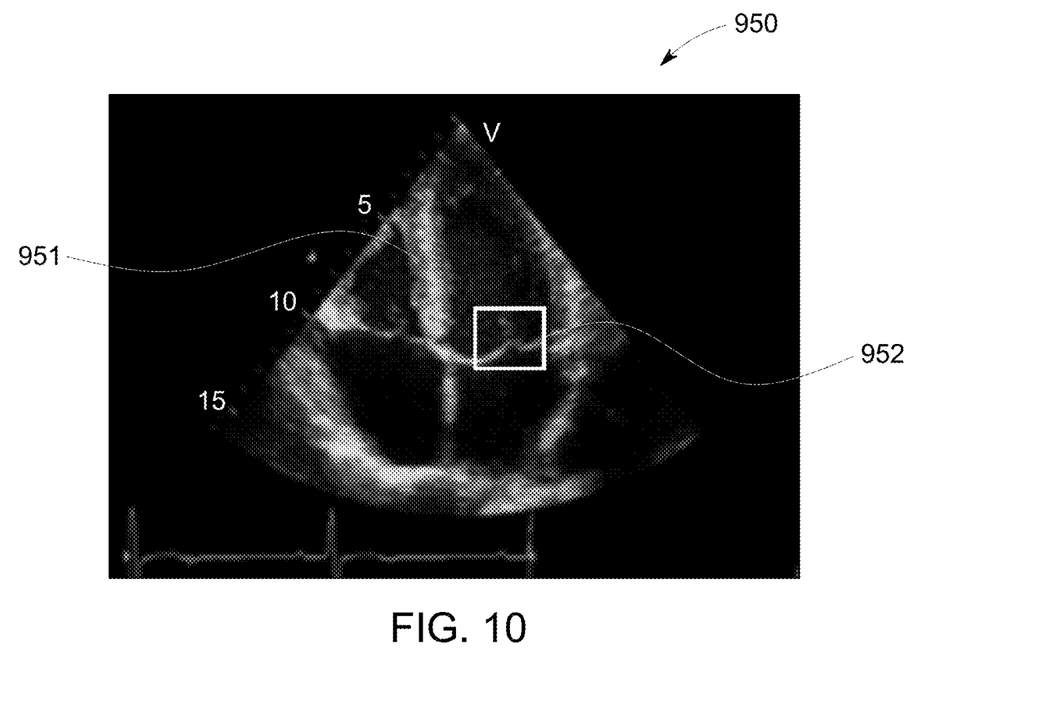
FIG. 10 is a screenshot in accordance with an exemplary embodiment.

According to an embodiment, the processor 116 may automatically place a region-of-interest with respect to the ultrasound image. The region-of-interest may be a 2D region-of-interest, a 3D region-of-interest, or a 4D region-of-interest according to various embodiments. The region-of-interest may be automatically placed in order to indicate a region from which a different mode of ultrasound data is to be acquired. For example, the region-of-interest may be a color box used to indicate an area from which color or Doppler ultrasound data is to be acquired, or the region-of-interest may be a Doppler gate to indicate a region from which pulsed wave (PW) Doppler data should be acquired. For example, FIG. 10 shows a screenshot 950 according to an embodiment. The screenshot 950 includes an ultrasound image 951 and an ROI box 952 positioned on the image 951. The ultrasound image 951 is a four-chamber view and the ROI box 952 has been automatically placed around the mitral valve by the processor 116. While FIG. 10 uses the ROI box 902 to represent the position of the region-of-interest, it should be appreciated that in other embodiments the region-of-interested may be automatically placed by the processor 116 without physically positioning an ROI box or other ROI graphical indicator on the image.

According to other embodiments, the low-resolution volume data may be used to identify a zoom region. For example, the low-resolution volume data may be used to identify a 2D zoom region or a 3D zoom region. The processor 116 may be configured to use image processing techniques in order to use the low-resolution volume data to identify one or more regions and then automatically place the 2D or 3D zoom around the one or more regions identified using the low-resolution volume data. For example, the processor 116 may use the low-resolution volume data to automatically zoom-in on a structure of interest. According to other embodiments, the processor 116 may implement one or more neural networks in order to automatically identify the one or more structures of interest in the low-resolution volume data and or to position the 2D zoom region or the 3D zoom region around the identified structure/s of interest. According to an embodiment, the processor 116 may be configured to display a candidate zoom box for either the 2D zoom region or the 3D zoom region on the ultrasound image generated from the high-resolution slice data. An operator would then, for instance, have the option to accept the candidate zoom box or make an adjustment to the candidate zoom box before accepting the zoom box. According to an embodiment, the processor 116 may display a box around the candidate 2D zoom region in the ultrasound image and the processor 116 may display a representation of a 3D box around the candidate 3D zoom region. It should be appreciated by those skilled in the art that other geometric shapes may be used to indicate the candidate zoom region according to various embodiments.

Figure 11:
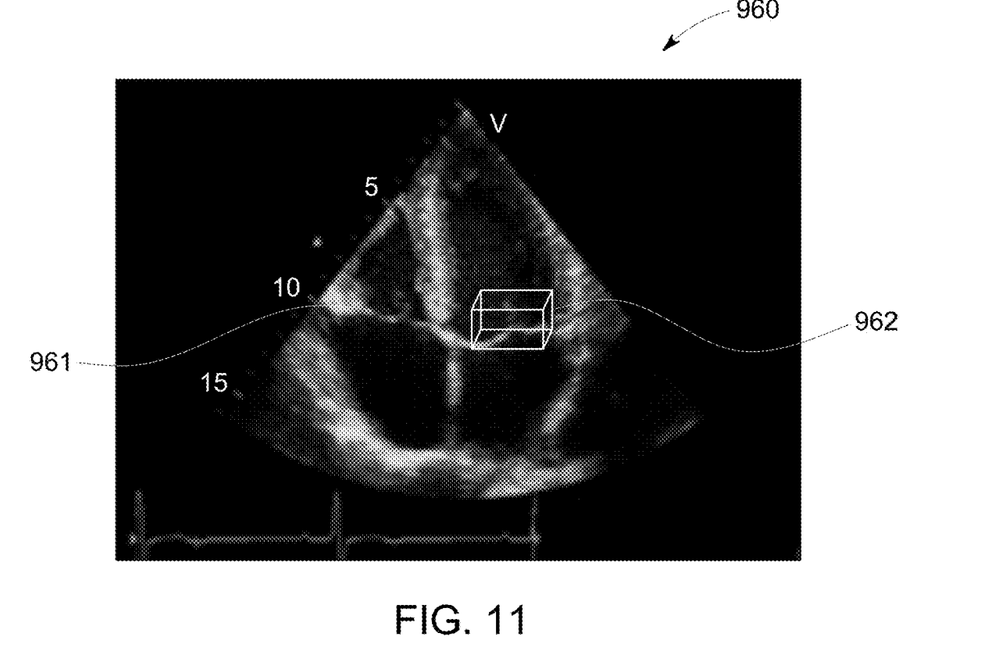
FIG. 11 is a screenshot in accordance with an embodiment.

FIG. 11 is a screenshot 960 according to an embodiment. The screenshot 960 includes an ultrasound image 961 and a representation of a 3D box 962 around a candidate 3D zoom region. The processor 116 is configured to zoom in on the 3D zoom region indicated by the position of the representation of the 3D box 962.

The processor 116 may be configured to display a model of the patient's anatomy at the same time as the ultrasound image generated based on the high-resolution slice data. The processor 116 may be configured to display a representation of the plane with respect to the model. According to an embodiment, the processor 116 may use the low-resolution volume data to register the position of the ultrasound probe 106 to the model. Then, the processor 116 may display the representation of the plane with respect to the model. For most embodiments, it is anticipated that the resolution of a rendering generated from the low-resolution volume data would be too low for displaying. Registering the low-resolution volume data to a model allows for the display of a much more visually pleasing representation of the patient's anatomy than would be possible by displaying an image directly based on the low-resolution volume data. Additionally, by displaying a representation of the plane, the clinician is able to quickly and easily see the position of the plane from which the ultrasound image was acquired with respect to the patient's anatomy.

Figure 12:
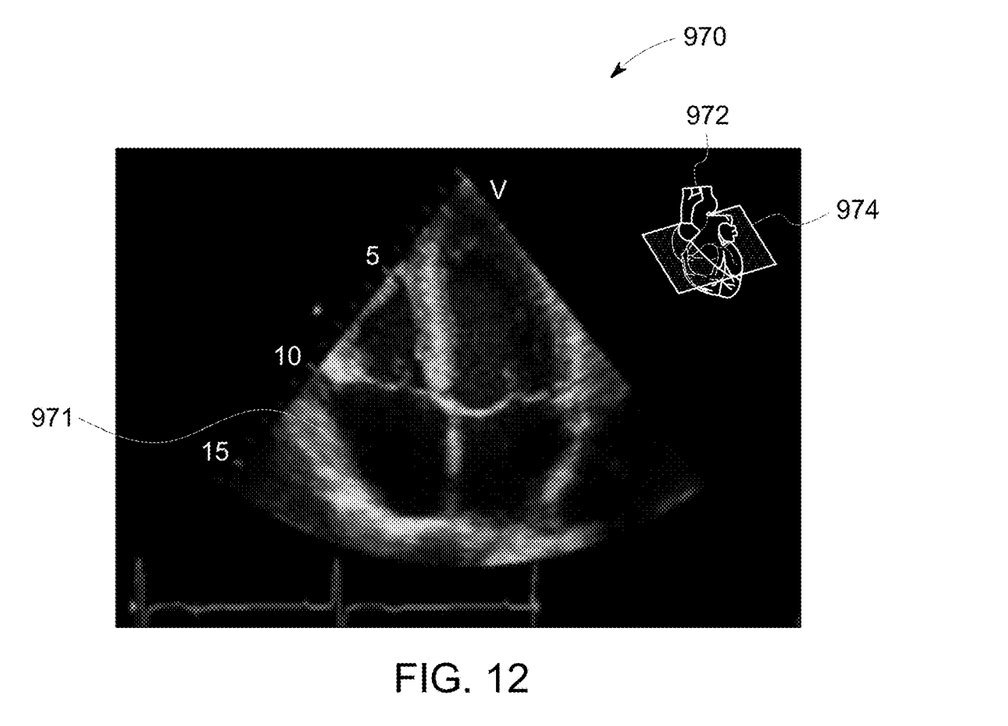
FIG. 12 is a screenshot in accordance with an embodiment.

FIG. 12 is a screenshot 970 according to an embodiment. The screenshot 970 includes an ultrasound image 971 and a model 972. According to an exemplary embodiment, the low-resolution volume data may be fit to the model 972 or registered to the model 972. The screenshot 970 also includes a representation of the plane 974. The representation of the plane 974 is shown in a position with respect to the model 972 to indicate the plane from which the image 971 was acquired from. The model 972 and the representation of the plane 974 may be used by the clinician to help correctly position the scan plane to acquire a desired anatomy or a desired view of the patient. In the example shown in FIG. 12, the model 972 is a model of a heart. The model 972 may be a rendered solid, a rendered wireframe, a rendered mesh, or it may be rendered by any other technique. The model 972 provides a higher resolution view of the heart than that which would possible by rendering the low-resolution volume data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of ultrasound imaging comprising:
acquiring low-resolution volume data with an ultrasound probe during the process of acquiring high-resolution slice data of a plane with the ultrasound probe, wherein the low-resolution volume data has a lower resolution than the high-resolution slice data;
displaying an ultrasound image on a display device based on the high-resolution slice data;
based on the low-resolution volume data, generating a low-resolution volume that is not displayed;
implementing, with a processor, a neural network to calculate guidance information based on the low-resolution volume; and
automatically performing at least one of the following actions with the processor based on the guidance information: displaying a guidance suggestion for adjusting the ultrasound probe in order to obtain a desired view; adjusting steering parameters of the ultrasound probe in order to acquire the desired view with the ultrasound probe in a current position and orientation; providing a warning that the ultrasound probe is incorrectly positioned; or automatically placing a region-of-interest with respect to the ultrasound image.

2. The method of claim 1, wherein the ultrasound image is a real-time ultrasound image based on the high-resolution slice data.

3. The method of claim 1, wherein the low-resolution volume data is acquired with less than 25 transmit events per volume.

4. The method of claim 3, wherein said acquiring the low-resolution volume data comprises transmitting defocused waves.

5. The method of claim 3, wherein said generating the low-resolution volume comprises at least one of applying nonlinear beamforming techniques to the low-resolution volume data or applying a massively multiline beamforming technique with 64 or more receive lines per transmit line.

6. The method of claim 1, wherein said implementing the neural network to calculate the guidance information comprises implementing the neural network to identify the desired view based on the low-resolution volume, and wherein said automatically performing at least one of the following actions comprises displaying the guidance suggestion for adjusting the ultrasound probe in order to obtain the desired view.

7. The method of claim 1, wherein said implementing the neural network to calculate the guidance information comprises implementing the neural network to identify the desired view based on the low-resolution volume, and wherein said automatically performing at least one of the following actions comprises adjusting the steering parameters of the ultrasound probe in order to acquire the desired view with the ultrasound probe in the current position and orientation.

8. The method of claim 1, wherein said implementing the neural network to calculate the guidance information comprises implementing the neural network to identify the desired view based on the low-resolution volume, and wherein said automatically performing at least one of the following actions comprises providing the warning that the ultrasound probe is incorrectly positioned.

9. The method of claim 8, wherein the ultrasound image is a cardiac ultrasound image and the desired view is an apical view, and wherein the warning comprises a notification than the ultrasound image being displayed has been foreshortened.

10. The method of claim 1, wherein said implementing the neural network to calculate the guidance information comprises implementing the neural network to identify the desired view based on the low-resolution volume, and wherein said automatically performing at least one of the following actions comprises automatically placing the region-of-interest with respect to the ultrasound image to include a desired region.

11. The method of claim 1, wherein said acquiring low-resolution volume data with the ultrasound probe comprises interleaving a first plurality of transmit events used to acquire the low-resolution volume data with a second plurality of transmit events used to acquire the high-resolution slice data.

12. The method of claim 1, wherein the high-resolution slice data comprises a plurality of frames of 2D ultrasound data, and wherein said acquiring the low-resolution volume data comprises acquiring a frame of the low-resolution volume data in between two adjacent frames of the plurality of frames of 2D ultrasound data.

13. An ultrasound imaging system comprising:
an ultrasound probe;
a user interface;
a display device; and
a processor in electronic communication with the ultrasound probe, the user interface and the display device, wherein the processor is configured to:
control the ultrasound probe to acquire low-resolution volume data during the process of acquiring high-resolution slice data of a plane, wherein the low-resolution volume data has a lower resolution than the high-resolution slice data;
display an ultrasound image on the display device based on the high-resolution slice data;
generate a low-resolution volume based on the low-resolution volume data, wherein the low-resolution volume is not displayed;
implement a neural network to calculate guidance information based on the low-resolution volume; and
automatically perform at least one of the following actions based on the guidance information: display a guidance suggestion for adjusting the ultrasound probe in order to obtain a desired view; adjust steering parameters of the ultrasound probe in order to acquire the desired view with the ultrasound probe in a current position and orientation; provide a warning that the ultrasound probe is incorrectly positioned; or place a region-of-interest with respect to the ultrasound image.

14. The ultrasound imaging system of claim 13, wherein the ultrasound image is a real-time ultrasound image.

15. The ultrasound imaging system of claim 13, wherein the low-resolution volume data is acquired with less than 25 transmit events per volume.

16. The ultrasound imaging system of claim 13, wherein the processor is configured to acquire the low-resolution volume data by transmitting defocused waves.

17. The ultrasound imaging system of claim 13, wherein said implementing the neural network to calculate the guidance information comprises identifying the desired view based on the low-resolution volume, and wherein the processor is configured to automatically perform the action of displaying the guidance suggestion for adjusting the ultrasound probe in order to obtain the desired view.

18. The ultrasound imaging system of claim 13, wherein said implementing the neural network to calculate the guidance information comprises identifying the desired view based on the low-resolution volume, and wherein the processor is configured to automatically perform the action of adjusting the steering parameters of the ultrasound probe in order to acquire the desired view with the ultrasound probe in a current position and orientation.

19. The ultrasound imaging system of claim 13, wherein said implementing the neural network to calculate the guidance information comprises identifying the desired view based on the low-resolution volume, wherein the processor is configured to determine that the ultrasound probe is incorrectly positioned based on the desired view, and wherein said automatically performing at least one of the following actions comprises providing the warning that the ultrasound probe is incorrectly positioned.

20. The ultrasound imaging system of claim 13, wherein said implementing the neural network to calculate the guidance information comprises identifying a desired region-of-interest from the low-resolution volume and wherein said automatically performing at least one of the following actions comprises automatically placing the region-of-interest with respect to the ultrasound image to include the desired region-of-interest.

21. The ultrasound imaging system of claim 13, wherein the low-resolution volume data is acquired with 16 transmit events or less.

22. The ultrasound imaging system of claim 13, wherein the low-resolution volume data is acquired with 4 transmit events or less per volume.

23. The ultrasound imaging system of claim 22, wherein the low-resolution volume data is acquired with a frame rate between 0.25 and 10 frames-per-second.

24. The ultrasound imaging system of claim 13, wherein the low-resolution volume data is acquired with 1 transmit event per volume.

25. The ultrasound imaging system of claim 13, wherein the low-resolution volume data is acquired with a frame rate between 0.25 and 10 frames-per-second.

* * * * *